United States Patent [19]

Kumar et al.

[11] Patent Number: 5,292,736

[45] Date of Patent: Mar. 8, 1994

[54] MORPHOLINOALKYLINDENES AS ANTIGLAUCOMA AGENTS

[75] Inventors: Virendra Kumar, Colonie; Susan J. Ward, East Greenbush, both of N.Y.

[73] Assignee: Sterling Winthrop Inc., New York, N.Y.

[21] Appl. No.: 23,452

[22] Filed: Feb. 26, 1993

[51] Int. Cl.[5] .......................................... A61K 31/535
[52] U.S. Cl. .............................. 514/231.5; 514/233.5; 514/233.8; 514/235.2; 514/235.8; 514/236.8; 514/239.5; 544/158
[58] Field of Search ............. 514/235.2, 233.5, 235.8, 514/233.8, 236.8, 231.5, 239.5

[56] References Cited

U.S. PATENT DOCUMENTS 3,532,752 10/1970 Shen .
3,622,623 11/1971 Shen et al. .
3,654,349 4/1972 Shen et al. .
4,044,040 8/1977 Hauck et al. .

Primary Examiner—Robert W. Ramsuer
Attorney, Agent, or Firm—Richard A. Hake; Paul E. Dupont

[57] ABSTRACT

Compounds of the formula

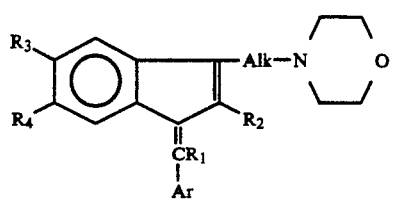

Formula I wherein
  Alk is lower-alkylene;
  $R_1$ is hydrogen, lower-alkyl, Ar or ArCOO;
  $R_2$ is hydrogen or lower-alkyl;
  $R_3$ and $R_4$ are the same or different hydrogen, fluoro, chloro, bromo, hydroxy, lower-alkoxy, lower-alkyl, or trifluoromethyl;
  Ar is phenyl, naphthyl, anthryl, 2-phenylethenyl or a 5- or 6-membered monocyclic or 9- or 10-membered bicyclic fused aromatic heterocyclic ring containing carbon and one or two heteroatoms independently selected from oxygen, nitrogen and sulfur, or such carbocyclic or heterocyclic rings substituted with from 1 to about 3 of lower-alkoxy, lower-alkyl, lower-alkylthio, lower-alkyl sulfinyl, lower-alkyl sulfonyl, hydroxy, cyano, amino, lower-alkylamino, dilower-alkylamino or halo;
or pharmaceutically acceptable acid addition salts thereof are useful as analgesics and in the treatment of glaucoma.

5 Claims, No Drawings

MORPHOLINOALKYLINDENES AS ANTIGLAUCOMA AGENTS

BACKGROUND OF THE INVENTION a) Field of the Invention

This invention relates to morpholinoalkylindenes, which are useful in the treatment of glaucoma, pharmaceutical compositions containing compounds of the invention and methods for use thereof in treating glaucoma.

b) Information Disclosure Statement

Shen U.S. Pat. No. 3,532,752, issued Oct. 6, 1970 discloses 1-alkylidene-3-indenyl aliphatic amines of the general formula

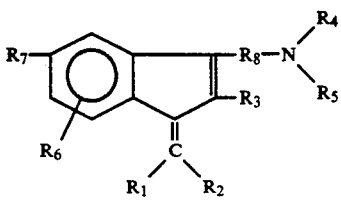

wherein $R_1$ and $R_2$, which may be the same or different, are each hydrogen or an alkyl, aryl or aralkyl radical, preferably lower-alkyl, aryl or ar-lower-alkyl containing functional substituents such as hydroxy halo, lower-alkylthio, lower-alkyl, trifluoromethyl, lower-alkylsulfamyl, lower-alkoxy, di(lower-alkyl)sulfamyl, nitro, phenyl and the like;

$R_3$ is hydrogen, halogen, hydroxy or a lower-alkyl, aryl, ar-lower-alkyl, lower-alkoxy, halo lower-alkyl, lower-alkylthio, arylthio, lower-alkenyl or lower alkoxyphenyl radical;

$R_4$ and $R_5$, which may be the same or different, are each hydrogen, lower-alkyl, halo lower-alkyl, lower-alkoxy lower-alkyl, hydroxy lower-alkyl, lower-alkenyl, lower-alkynyl, cyclopropyl lower-alkyl, tetrahydrofurfuryl, cyclic lower-alkyl, or together with the nitrogen to which they are attached, morpholino, piperidino, piperazino, substituted piperazino such as N-phenylpiperazino, N-hydroxyethylpiperazino and N-methylpiperazino, pyrrolidino and 1,2,5,6-tetrahydropyridino radicals;

$R_6$ is hydrogen, halogen, lower-alkyl, lower-alkoxy, alkylthio, aryl, aryloxy or trifluoromethyl and together with $R_7$ when they are ortho to each other lower-alkyenedioxy;

$R_7$ is hydrogen, hydroxy, lower-alkyl, lower-alkoxy, nitro, amino, lower-alkylamino, di(lower-alkyl)amino, loweralkanoylamino, lower-alkanoyl, bis(hydroxy lower-alkyl)amino, 1-pyrrolidino, 4-methyl-1-piperazinyl, 4-morpholinyl, alkylsulfonyl, cyano, trifluoromethyl halogen, di(loweralkyl)sulfamyl, benzylthio, benzyloxy, lower-alkylbenzyloxy, lower-alkoxybenzyloxy, halogenbenzyloxy, lower-alkenyl, loweralkenyloxy, 1-azacyclopropyl, cyclopropyl lowered alkoxy, cyclobutyl lower alkoxy and together with $R_6$ when they are ortho to each other, lower alklenedioxy;

$R_8$ is one of the following groups:

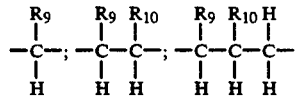

in which $R_9$ and $R_{10}$, which may be same or different, are each hydrogen, lower-alkyl, halo lower-alkyl, benzyloxy lower-alkyl, hydroxy lower-alkyl, lower-alkenyl, phenyl or lower-alkynl. The compounds are stated to be useful as antiinflammatory and antipyretic agents.

Shen et al. U.S. Pat. No. 3,622,623, issued Nov. 23, 1971 discloses

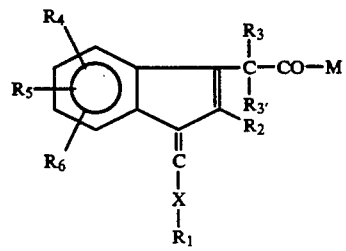

in which $R_1$ may be aryl or heteroaryl;

X may be alkylene or alkenylene;

$R_2$ may be hydrogen, alkyl, aralkyl, aryl, heteroaryl, halogen, hydroxy, alkoxy, haloalkyl, alklthio, and arylthio;

$R_3$ may be hydrogen, lower-alkyl, halo lower-alkyl, fluorine, amino acylamino, dialkylamino, N-morpholino, alkenyl, aralkylthio, hydroxy and alkoxy and together with $R_3'$ a methylene;

$R_4$, $R_5$ and $R_6$ each may be hydrogen, alkyl, alkoxy, nitro, amino, acylamino, alkylamino, dialkylamino, dialkylaminoalkyl, sulfamyl, alkylthio, mercapto, alkyl-sulfonyl, arylsulfonyl, halogen, cyano, carboxyl, carbalkoxy, carbamido, aryl, halogenoalkyl, alkenoxy, aryloxy, alkenyl, aryloxy, cycloalkyl and cycloalkyloxy, and M may be hydroxy, lower-alkoxy, substituted lower-alkoxy, amino, alkylamino, dialkylamino, N-morpholino, hydroxyalkylamino, polyhydroxyalkylamino, dialkylaminoalkylamino, aminoalkylamino, and the group OMe in which Me is a cation as well as the 2,3-dihydro derivatives of said compounds. These compounds are stated to be useful as analgesics, anti-inflammatory and antipyretic agents.

Shen et al. U.S. Pat. No. 3,654,349, issued Apr. 4, 1972 discloses compounds of the formula

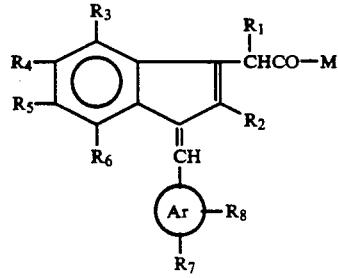

wherein

Ar may be aryl or hetaryl;

$R_1$ may be hydrogen, lower-alkyl or halogenated lower-alkyl;

$R_2$ may be hydrogen or alkyl;

$R_3$, $R_4$, $R_5$ and $R_6$ each may be hydrogen, alkyl, aclyoxy, alkoxy, nitro, amino, acylamino, alkylamino, dialkylamino, dialkylaminoalkyl, sulfamyl, alkythio, mercapto, hydroxy, hydroxyalkyl, alkylsulfonyl, halogen, cyano, carboxyl, carbalkoxy, carbamido, halogenoalkyl, cycloalkyl or cycloalkoxy;

$R_7$ may be alkylsulfinyl or alkylsulfonyl;

$R_8$ may be hydrogen, halogen, hydroxy, alkoxy, or haloalkyl; and

M may be hydroxy, lower-alkoxy, substituted loweralkoxy, amino, alkylamino, dialkylamino, N-morpholino, hydroxyalkylamino, polyhydroxyalkylamino, dialkylaminoalkylamino, aminoalkylamino, and the group OMe, in which Me is a cation.

The compounds are stated to have antiinflammatory, antipyretic and analgesic activity.

Hauck et al. U.S. Pat. No. 4,044,040, issued Aug. 27, 1977, discloses 1-[3-(3-indenyl)propyl]morpholine as an intermediate in the preparation of 4,7-dihydroindenylalkanols and their analogues, stated to be useful in the treatment of hypertension.

SUMMARY OF THE INVENTION

It has been found that morpholinoalkylindenes are useful as analgesics and are cannabinoid agonists and as such are useful in the treatment of glaucoma.

Accordingly, this invention relates to morpholinoalkylindenes of the formula

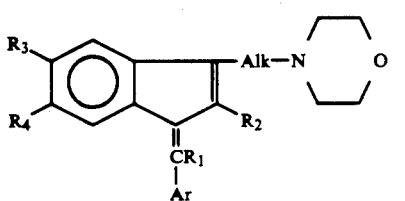

Formula I wherein

Alk is lower-alkylene;

$R_1$ is hydrogen, lower-alkyl, Ar or ArCOO;

$R_2$ is hydrogen or lower-alkyl;

$R_3$ and $R_4$ are the same or different hydrogen, fluoro, chloro, bromo, hydroxy, lower-alkoxy, lower-alkyl, or trifluoromethyl;

Ar is phenyl, naphthyl, anthryl, 2-phenylethenyl or a 5- or 6-membered monocyclic or 9- or 10-membered bicyclic fused aromatic heterocyclic ring containing carbon and one or two heteroatoms independently selected from oxygen, nitrogen and sulfur, or such carbocyclic or heterocyclic rings substituted with from 1 to about 3 of lower-alkoxy, lower-alkyl, lower-alkylthio, lower-alkyl sulfinyl, lower-alkyl sulfonyl, hydroxy, cyano, amino, lower-alkylamino, dilower-alkylamino or halo;

or pharmaceutically acceptable acid addition salts thereof.

Falling within the ambit of this invention are compositions for the relief of pain containing an analgesically effective amount of a morpholinoalkylindene of formula I.

In a further composition aspect, the invention relates to compositions for lowering intraocular pressure related to glaucoma, containing an effective amount of a morpholinoakylindene of formula I.

In a method of use aspect, the invention relates to a method for treatment of pain which comprises administering to one in need of such treatment an effective amount of a morpholinoalkylindene of formula I.

In a further method of use aspect, the invention relates to a method for treatment of glaucoma which comprises administering to one in need of such treatment an effective amount of a morpholinoalkylindene of formula I.

DETAILED DESCRIPTION INCLUSIVE OF PREFERRED EMBODIMENTS

As used herein, unless otherwise specifically defined, the term lower-alkyl refers to a straight or branched monovalent hydrocarbon radical of from one to about four carbon atoms and includes for example, methyl, propyl, ethyl, n-butyl, secbutyl, and the like. Likewise, lower-alkoxy refers to a straight or branched alkoxy radical containing from 1 to about 4 carbon atoms, for example, methoxy, propoxy, ethoxy, n-butoxy, secbutoxy, and the like.

As used herein the term halide or halo refers to fluoro, chloro, bromo, and iodo.

As used herein the term lower alkylene refers to a straight or branched divalent hydrocarbon radical containing from about 2 to about 4 carbons, including, but not limited to ethylene, propylene, 1,2-dimethyl ethylene, 2-methyl-propylene, and the like.

Examples of a 5- or 6-membered monocyclic aromatic heterocyclic ring include pyridyl, furyl, imidazolyl, oxazolyl, thienyl, thiazolyl, pyrazinyl, pyrimidinyl and the like. A 9- or 10-membered bicyclic fused aromatic heterocyclic ring is exemplified by benzimidazolyl, quinolyl, benzofuranyl, indolyl and the like.

Preferred compounds of formula I are compounds wherein Alk is 1,2-ethylene or 1,3-propylene and $R_1$ is methyl or hydrogen and $R_3$ and $R_4$ are hydrogen.

Compounds used as starting materials in the synthesis of compounds of formula I are known compounds or come from families of known compounds and can be prepared by methods well known in the art.

Compounds of formula I are prepared by reaction of the indene II

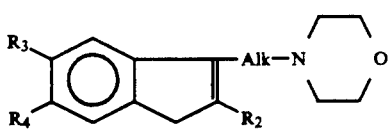

II with a strong base such as sodium methoxide, n-butyllithium and the like, followed by addition of the appropriate aldehyde, ketone or acid halide of formula III

III wherein $R_1$ is hydrogen, lower-alkyl, Ar, or chloro, bromo or iodo, preferably in an inert solvent at a temperature between ambient and the boiling point of the solvent.

It will be appreciated that in the reaction of indene II with an acid halide of formula III, two equivalents of the acid halide may be used to prepare compounds of formula I where $R_1$ is ArCOO. Presumably the initially formed acyl indene reacts with a second equivalent of the acid halide giving compounds of formula I where $R_1$ is ArCOO.

The indene of formula II is prepared by alkylation of the known indene IV:

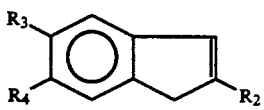

treatment with a strong base, e.g. sodium methoxide, n-butyllithium and the like, preferably under inert atmosphere and in an inert solvent at a temperature between ambient and the boiling point of the solvent. After the reaction with base, the appropriate morpholinoalkyl halide V:

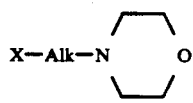

wherein X is a leaving group, for example, chloro, bromo, iodo, or tosyl, is added in roughly equimolar amount at a temperature between about 0° C. and the boiling point of the reaction mixture, preferably under an inert atmosphere yielding a compound of formula II.

The preparation of indenes of formula IV is described in detail in U.S. Pat. No. 3,532,752, which is incorporated herein by reference, and the morpholinoalkyl halides of formula V are generally known or can be prepared by methods well known in the art.

It will be appreciated that the double bond, bearing $R_1$ and Ar, in the compounds of formula I, may exist in either the E or Z isomeric configuration. In some cases, there may be an advantage to using one or the other isomer for treatment of pain or glaucoma. Isomers may be separated by methods well known in the art, such as fractional crystallization or chromatography.

The compounds of the invention are sufficiently basic to form acid-addition salts, and are useful both in the free base form and the form of acid-addition salts, and both forms are within the purview of the invention. The acid-addition salts are in some cases a more convenient form for use, and in practice the use of the salt form inherently amounts to the use of the base form. The acids which can be used to prepare the acid-addition salts include preferably those which produce, when combined with the free base, medicinally acceptable salts, that is, salts whose anions are relatively innocuous to the animal organism in medicinal doses of the salts so that the beneficial properties inherent in the free base are not vitiated by side effects ascribable to the anions.

Examples of appropriate acid-addition salts include but are not limited to the hydrochloride, hydrobromide, sulfate, acid sulfate, maleate, citrate, tartrate, methanesulfonate, p-toluenesulfonate, dodecyl sulfate, cyclohexanesulfamate, and the like. However, other appropriate medicinally acceptable salts within the scope of the invention are those derived from other mineral acids and organic acids. The acid-addition salts of the basic compounds are prepared either by dissolving the free base in aqueous alcohol solution containing the appropriate acid and isolating the salt by evaporating the solution, or by reacting the free base and an acid in an organic solvent, in which case the salt separates directly, is precipitated with a second organic solvent, or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate products, as, for example, when the salt is formed only for purposes of purification or identification, or when it is used as an intermediate in preparing a medicinally acceptable salt by ion exchange procedures.

The structures of the compounds of the invention were established by the mode of synthesis, by elemental analysis, and by infrared spectroscopy. In certain cases, ultraviolet, nuclear magnetic resonance or mass spectroscopy were used to characterize products. The course of the reactions was assessed by thin layer chromatography (TLC) or gas-liquid chromatography (GLC).

The following examples will further illustrate the invention without, however, limiting it thereto. Starting materials for the synthesis of compounds of formula I are known, come from families of known compounds, are commercially available or prepared by methods well known in the art.

PREPARATION OF INTERMEDIATES

Preparation 1

2-methyl-3-[2-(4-morpholinyl)ethyl]indene 16.4 g (0.126 mol) 2-methylindene was taken up in 150 ml dry ether under nitrogen atmosphere. A solution of 9.6 g (0.15 mol) n-butyl lithium (2.1 M) in hexane (62 ml) was added dropwise to the indene/ether solution. The resulting solution was stirred at room temperature for 2 hours and a solution of 3.5 g (0.18 mol) N-(2-chloroethyl)morpholine in 100 ml ether was added and stirred overnight. Saturated solution of ammonium chloride was added to the reaction mixture and the ether layer was extracted with 2N HCl. The acidic aqueous layer was then washed with ether twice and cooled in an ice bath, then neutralized with 35% sodium hydroxide and extracted with ether to give 16.3 g (54%) of the 2-methyl-3-(2-ethyl N-morpholinyl)indene (Formula II $R_z$=methyl; $R_3$=$R_4$=hydrogen; Alk=1,2-ethylene).

Preparation 2

3-[2-(4-morpholinyl)ethyl]indene 5.8 g (0.05 mol) indene was taken up in 50 mL dry ether under nitrogen. To this solution a solution of 2.303 g (0.05 mol) n-butyllithium (2.1 M) in 150 mL of ether was added dropwise. The solution was stirred at room temperature for 2 hours and a solution of 33.5 g (0.18 mol) N-(2-chloroethyl)morpholine was added and stirred overnight at room temperature. The reaction mixture was neutralized with saturated ammonium chloride solution and the ether layer separated and dried over magnesium sulfate and concentrated in vacuo giving a yellow oil. The product was redissolved in ether and extracted with 200 ml 2 N HCl twice. The aqueous layer was again extracted with ether and cooled in an ice bath. This cooled, acidic mixture was then slowly neutralized with 35% NaOH and extracted twice with ether. The organic layers were pooled and washed with water, saturated NaCl and dried over magnesium sulfate to give 6.9 g (60%) of the desired 3-[2-(4-morpholinyl)ethyl]indene (Formula II $R_2$=$R_3$=$R_4$=hydrogen; Alk=1,2-ethylene).

Preparation 3

3-[3-(4-morpholinyl)propyl]indene

This compound (Formula II: $R_2=R_3=R_4=H$, Alk=1,3-propylene) was prepared as described in U.S. Pat. No. 4,044,040, which is incorporated herein by reference.

It will be appreciated that the formula IV indenes disclosed in U.S. Pat. No. 3,532,752 include such species as:

5,6-dimethylindene
2-methyl-5,6-fluoro,6-chloroindene
6-trifluoromethylindene
2-ethyl-5,6-dimethoxyindene
5-hydroxy-6-methylindene and that it is contemplated that these formula IV indenes are alkylated with an appropriate morpholinoalkyl halide of formula V by a method substantially as described in Preparation 1 or 2.

These intermediate indenes of formula II were then reacted with a strong base, and an aldehyde, ketone or acid halide of formula III as described below to afford compounds of formula I. It will be appreciated that these compounds are illustrative examples and do not limit the invention thereto.

PREPARATION OF COMPOUNDS OF FORMULA I

Example 1

Preparation of 4-[2-[1-[(4-methoxyphenyl)methylene]-1H-inden-3-yl)ethyl]morpholine (Formula I: $R_1=R_2=R_3=R_4$=hydrogen, Alk=1,2-ethylene, Ar=4-CH$_3$OC$_6$H$_4$)

To a solution of 12.6 g of the product of preparation 2 in 120 ml methanol, was added 6.6 g sodium methoxide, immediately after this addition 9.06 g p-anisaldehyde was added. The reaction mixture was then refluxed on a steam bath for 8 hours, cooled and poured into an ice bath, the aqueous layer was neutralized with saturated ammonium chloride solution and then extracted with 200 ml methylene chloride thrice. The organics were then pooled and washed with water until neutral, dried over magnesium sulfate and concentrated in vacuo. The dried product was taken up in ether and washed thrice with 200 ml 2 N HCl The combined acidic layers were then combined and washed with ether. The acidic solution was neutralized with 35% NaOH in an ice bath and the product was extracted into methylene chloride, washed with water, then brine, dried over magnesium sulfate, and concentrated in vacuo, yielding a yellow oil containing the desired compound of formula I. The oil was taken up in methylene chloride, and excess maleic acid was added, 20.7 g of the maleate salt was collected by filtration (76%), mp 175°–177° C.

In the tabulation below, the listed gram amount of the appropriate formula I indene was reacted with the gram amount of the appropriate compound of formula III, and the mixture refluxed for the listed amount of time in a reaction scheme substantially as described above. The overall yields shown reflect the yield of the final product that was then collected and characterized as the acid addition salt. In examples 2–20, the melting point is that of the HCl addition salt, obtained by adding ethereal HCl to the reaction product in methylene chloride and collected by filtration.

EXAMPLES

TABLE 1

Examples
Preparation of compounds of formula I

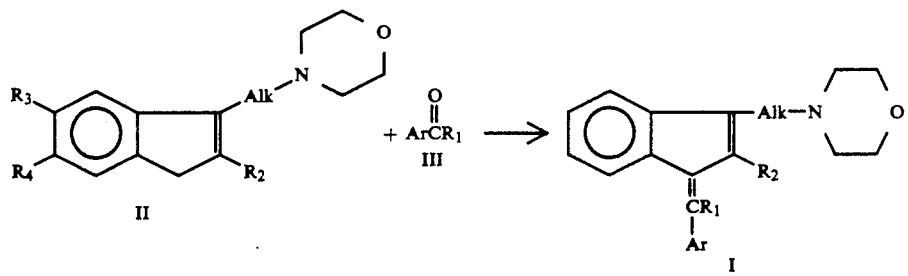

| Example | R$_2$/R$_3$/R$_4$ | Alk | Ar | R$_1$ | II/III (g) | Reflux Time | Yield (%) | melting point (°C.) |
|---|---|---|---|---|---|---|---|---|
| 2 | H/H/H | (CH$_2$)$_2$ | C$_6$H$_5$ | H | 6.37/12.1 | 6 h | ND | 197–199 |
| 3 | CH$_3$/H/H | (CH$_2$)$_2$ | 4-CH$_3$OC$_6$H$_4$ | H | 10.7/16.0 | 6 h | 28 | 230–232 |
| 4 | H/H/H | (CH$_2$)$_2$ | 4-CH$_3$SC$_6$H$_4$ | H | 9.13/11.4 | 6 h | 78 | 233–235 |
| 5 | H/H/H | (CH$_2$)$_3$ | 4-FC$_6$H$_4$ | H | 11.7/20.0 | 18 h | 27 | 215–217 |
| 6 | H/H/H | (CH$_2$)$_2$ | 4-(CH$_3$)$_2$NC$_6$C$_4$ | H | 8.95/11.6 | 6 h | 13 | 146–148 |
| 7 | H/H/H | (CH$_2$)$_2$ | 2-FC$_6$H$_4$ | H | 1.1/10.6 | 6 h | 81 | 214–216 |
| 8 | H/H/H | (CH$_2$)$_2$ | 4-CH$_3$O-1-naphthyl | H | 10.4/11.45 | 6 h | 52 | 249–251 |
| 9 | H/H/H | (CH$_2$)$_2$ | 1-naphthyl | H | 9.4/11.4 | 6 h | 40 | 206–208 |
| 10 | CH$_3$/H/H | (CH$_2$)$_2$ | 1-naphthyl | H | 4.4/6.3 | 6 h | 92 | 282–284 |
| 11 | CH$_3$/H/H | (CH$_2$)$_2$ | 4-quinolyl | H | 7.2/11.4 | 8 h | 45 | 168–170 |
| 12 | H/H/H | (CH$_2$)$_3$ | 1-naphthyl | H | 7.3/11.5 | 8 h | 55 | 119–121 |
| 13 | H/H/H | (CH$_2$)$_2$ | 3,4-(CH$_3$O)$_2$C$_6$H$_3$ | H | 7.9/12.0 | 18 h | 37 | 199–201 |
| 14 | H/H/H | (CH$_2$)$_2$ | C$_6$H$_5$CH=CH— | H | 6.7/11.4 | 8 h | 39 | 122–124 |
| 15 | H/H/H | (CH$_2$)$_3$ | 4-CH$_3$O-1- | H | 6.5/12.0 | 8 h | 45 | 172–174 |

TABLE 1-continued

| | | | | | | | | |
|---|---|---|---|---|---|---|---|---|
| 16 | CH$_3$/H/H | (CH$_2$)$_2$ | 4-CH$_3$O-1-naphthyl | H | 6.5/12.3 | 8 h | 32 | 265–267 |
| 17 | H/H/H | (CH$_2$)$_2$ | 4-CN—C$_6$H$_4$ | H | 6.5/12.4 | 18 h | 51 | 223–225 |
| 18 | H/H/H | (CH$_2$)$_2$ | 4-indolyl | H | 10.3/11.7 | 18 h | 42 | 143–145 |
| 19 | H/H/H | (CH$_2$)$_2$ | 4-HO-1-naphthyl | H | 6.7/11.2 | 8 h | 53 | 219–221 |
| 20 | H/H/H | (CH$_2$)$_2$ | 9-anthryl | H | 12.4/12.4 | 18 h | 70 | 170–172 |

EXAMPLE 21

Preparation of 4-[2-[[1-[4-(methylsulfinyl)phenyl]methylene]-1H-inden-3-yl]ethyl]morpholine To a solution of 19 g sodium metaperiodate and 20 ml water was added a suspension of 3.4 g (8.5 mmol) of example compound 4 (formula 1 R$_1$=R$_2$=R$_3$=R$_4$=hydrogen, m=O, Alk=1,2-ethylene, Ar=4CH$_3$SC$_6$H$_4$) in 30 ml methanol. The reaction mixture was stirred at room temperature for 4 hours, and the solid filtered off, washed with water, and the solution evaporated to dryness. The residue was taken up in methylene chloride and washed with ammonium hydroxide, dried over magnesium sulfate and concentrated in vacuo to give 3.1 g of a compound of formula 1 (R$_1$=R$_2$=R$_3$=R$_4$=hydrogen, Ar=4-CH$_3$SOC$_6$H$_4$, Alk=1,2-ethylene) as the free base. The HCl addition salt of this product was prepared described above and had a melting point of 122°–124° C.

Example 22

Preparation of (4-methoxyphenyl)[3-(2-[4-morpholinyl)ethyl)-1H-inden-1-ylidine]methyl 4-methoxy benzoate 20.09 g (87 mmol) 3-[(4-morpholinyl) 2-ethyl]indene was added to a solution of 11.2 g (175 mmol) n-Butyl lithium (2.1 M) in 300 ml ether. To this solution 30.7 g (180 mmol) of p-anisoyl chloride in 100 ml ether was added and stirred for 30 minutes. The reaction mixture was neutralized with saturated ammonium chloride solution and the ether layer was separated and dried over magnesium sulfate, and concentrated in vacuo to an oil. The oil was taken up in methylene chloride and washed with saturated ammonia, and passed through a fluorosil plug, and concentrated in vacuo to give 36.8 g of a gum, which is a compound of formula I (Formula 1 R$_2$=R$_3$=R$_4$=hydrogen, R$_1$=panisoyloxy, Alk=1,2-ethylene, Ar=p-methoxyphenyl). The HCl addition salt of this product, prepared as above, had a melting point of 213°–215° C.

It is contemplated that any of the following compounds of formula III can be reacted with an indene of formula II by the method described in example 1 to give the corresponding compounds of formula I:

| | I | |
|---|---|---|
| III | R1 | Ar |
| Benzofuran-2-carboxaldehyde | H | 2-benzofuryl |
| Pyrazine-2-carboxaldehyde | H | 2-pyrazinyl |
| 1-Methylpyrrole-2-carboxaldehyde | H | 1-methyl-2-pyrrolyl |
| Thiazole-2-carboxaldehyde | H | thiazolyl |
| Furan-2-carboxaldehyde | H | furyl |
| Thiophene-2-carboxaldehyde | H | thienyl |
| Benzophenone | phenyl | phenyl |
| 4'4'Methoxybenzophenone | 4-OCH$_3$phenyl | 4-OCH$_3$ phenyl |
| Propiophenone | CH$_2$CH$_3$ | phenyl |
| Acetophenone | CH$_3$ | phenyl |
| 1-Methylimidazole-2-carboxaldehyde | H | 1-methylimidazolyl |
| 1-Methylbenzimidazole-2-carboxaldehyde | H | 1-methylbenzimidazolyl |
| Benzothiazole-2-carboxaldehyde | H | 2-benzothiazolyl |
| Benzothiophene-2-carboxaldehyde | H | 2-benzothiophenyl |

It is further contemplated that reaction of an indene of formula II with the following acid halides of formula III, R$_1$=halogen, by the method of example 22 will afford corresponding compounds of formula I:

| | I | |
|---|---|---|
| III | R1 | Ar |
| 2-furoyl chloride | 2-furoyloxy | 2-furyl |
| benzoyl chloride | benzoyloxy | phenyl |
| 2-methoxybenzoyl chloride | 2-methoxybenzoyloxy | 2-methylphenyl |
| 1-naphthoyl chloride | 1-naphthoyloxy | 1-naphthyl |
| 4-fluorobenzoyl chloride | 4-fluorobenzoyloxy | 4-fluorophenyl |
| 2-thiophenecarbonyl chloride | 2-thenoyloxy | 2-thienyl |
| 2-thiazolecarbonyl chloride | 2-thiazolylcarbonyloxy | 2-thiazolyl |

Biological Test Results

In standard biological test procedures, compounds of formula I were tested for analgesic and cannabinoid receptor activity. The mouse vas deferens test correlates well with analgesic activity and has long been used to screen for such activity. Cannabinoid receptor binding is characteristic and predictive of the efficacy of intraocular pressure reducing compounds and was thus used to test the compounds of formula I for antiglaucoma activity.

The mouse vas deferens test (MVD), a means of screening for analgesic activity, is disclosed in U.S. Pat. No. 4,840,950, which is incorporated herein by reference. Data obtained in the mouse vas deferens test, expressed as the IC$_{50}$ in μM, for the compounds described above, identified by the example number where their preparations are described, are given in the table below. Compounds are considered active in the MVD test at IC$_{50}$ levels of 5.0 μM or less.

Data obtained by the oral administration of the invention in the acetylcholine-induced abdominal constriction test (ACH), a measure of analgesic effectiveness, are expressed in the table below as the ED$_{50}$ in mg/kg or as the percent inhibition at a given dose level in mg/kg. The acetyl choline-induced abdominal constriction test (ACH) is described in Brit. J. Pharmacol., 32: 295 (1968) and U.S. Pat. No. 4,581,534, incorporated herein by reference.

Data from the cannabinoid receptor binding test (CR), predictive of antiglaucoma activity, was obtained as follows:

Brain tissue from rats was homogenized in ice cold 20 mM HEPES-NaOH, pH 7.0, diluted approximately 1:100 (w/v) with the same buffer and centrifuged at 48,000 g for 10 minutes at 4° C. The pellet was washed by resuspension and centrifugation as above. The final pellet was suspended (1:120 w/v) in 20 mM HEPES-NaOH, pH 7.0 and stored on ice for use within 1 hour.

Compounds (10 mM) were solubilized in a mixture of 0.3 N methane sulfonic acid - 13.5% ethanol. Cannabinoids were dissolved in absolute ethanol. Other compounds were dissolved in dimethylsulfoxide (DMSO). All compounds were diluted in 20 mM HEPES, pH 7.0 containing 5 mg/ml bovine serum albumin (BSA).

The final assay concentration of BSA was 1.0 mg/ml in these experiments. Final assay concentrations of $\leq 50$ mM ethanol, $\leq 1 \times 10^{-3}$ N methane sulfonic acid, $\leq 2.5$ mM ethanol $+ 3 \times 10^{-4}$ N methane sulfonic acid or $\leq 3\%$ DMSO had no effect on specific binding. The possible effects of all vehicles were controlled in each assay.

The assay was started with the addition of homogenate and the tubes incubated at 30° C. for 90 min in a shaking waterbath. Each tube contained 20 mM HEPES-NaOH buffer, pH 7.0, 1.0 mg/ml BSA, competing drug or vehicle, and 100–125 μg membrane protein in a 1 ml incubation volume. Saturation studies were conducted over 3 log units of radioligand concentration (0.1–22 nM). Specific binding was defined as the difference in binding in the presence and absence of 1.0 μM unlabeled 2-[(3-chloro-4-hydroxyphenyl)amino]-benzene methanol, a molecule that is known to non-specifically bind to cannabinoid receptors.

Samples were filtered over Whatman GF/B filters with 20 ml of 20 mM HEPES, pH 7.0, containing 0.5 mg/ml BSA. Radioactivity on the filters, expressed in dpm, was measured by liquid scintillation spectrometry. Assays were conducted in triplicate and experiments were repeated at least three times.

The results for the CR test are $IC_{50}$ concentrations (in nM) or % inhibition at 1 μM and 30 μM concentrations.

TABLE II

| Example | MVD $IC_{50}$ (μM) | Ach | CR $IC_{50}$ | CR % @ 1 μM | CR % @ 30 μM |
|---|---|---|---|---|---|
| 1 | 0.08 | 46 | 58 | | |
| 2 | 0.079 | 65 | | 33 | |
| 3 | NT | 30% at 100 | | 45 | |
| 4 | NT | 50 | | 96 | |
| 5 | NT | 52 | | | 5 |
| 6 | NT | 103 | | | 88 |
| 7 | NT | 86 | | | 78 |
| 8 | 0.008 | 3.2 | 0.9 | | |
| 9 | 0.007 | 83% at 10 | 1.0 | | |
| 10 | 0.045 | 34 | 10.0 | | |
| 11 | 1.65 | 40% at 100 | NT | | |
| 12 | 0.096 | 30% at 100 | | 97 | |
| 13 | 0.019 | 19 | 28 | | |
| 14 | NT | 20% at 100 | | 68 | |
| 15 | NT | 10% at 100 | 12 | | |
| 16 | 0.35 | 30% at 100 | NT | | |
| 17 | NT | 100 | | 76 | |
| 18 | 0.31 | 15 | NT | | |
| 19 | NT | 2.7 | | 97 | |
| 20 | 0.812 | NT | NT | | |
| 21 | 0.193 | 25 | NT | | |
| 22 | NT | 10% at 100 | | 51 | |

NT = Not tested

The compounds of the invention can be prepared for pharmaceutical use by incorporation of the compounds in unit dosage form as tablets or capsules for oral or parenteral administration either alone or in combination with suitable adjuvants such as calcium carbonate, starch, lactose, talc, magnesium stearate, gum acacia and the like. Still further, the compounds can be formulated for oral, ocular, or parenteral administration either in aqueous solutions of the water-soluble salts or in aqueous alcohol, glycol or oil solutions or oil-water emulsions in the same manner as conventional medicinal substances are prepared.

The percentages of active component in such compositions may be varied so that a suitable dosage is obtained. The dosage administered to a particular patient is variable, depending upon the clinician's judgment using as criteria: the route of administration, the duration of treatment, the size and physical condition of the patient, the potency of the active component and the patient's response thereto. An effective dosage amount of the active component can thus be readily determined by the clinician after a consideration of all criteria and using his best judgment on the patient's behalf.

We claim:

1. A method for the treatment of glaucoma which comprises administering to a patient in need of such treatment a medicament containing an effective intraocular pressure reducing amount of a compound having the formula:

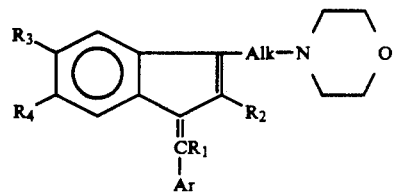

wherein
Alk is lower-alkylene;
$R_1$ is hydrogen, lower-alkyl, Ar or ArCOO;
$R_2$ is hydrogen or lower-alkyl;
$R_3$ and $R_4$ are the same or different hydrogen, fluoro, chloro, bromo, hydroxy, lower-alkoxy, lower-alkyl, or trifluoromethyl;
Ar is phenyl, naphthyl, anthryl, 2-phenylethenyl or a 5- or 6-membered monocyclic or 9- or 10-membered bicyclic fused aromatic heterocyclic ring containing carbon and one or two heteroatoms independently selected from oxygen, nitrogen and sulfur, or such carbocyclic or heterocyclic rings substituted with from 1 to about 3 of lower-alkoxy, lower-alkyl, lower-alkylthio, lower-alkyl sulfinyl, lower-alkyl sulfonyl, hydroxy, cyano, amino, lower-alkylamino, dilower-alkylamino or halo;
or phamaceutically acceptable acid addition salts thereof.

2. A method for the treatment of glaucoma which comprises administering to a patient in need of such treatment a medicament containing an effective intraocular pressure reducing amount of a compound according to claim 1 wherein;

$R_1$ is hydrogen and Alk is 1,2-ethylene or 1,3-propylene.

3. A method for the treatment of glaucoma which comprises administering to a patient in need of such treatment a medicament containing an effective intraocular pressure reducing amount of a compound according to claim 2 wherein;

Ar is phenyl or naphthyl or phenyl or naphthyl substituted by from 1 to 2 substituents selected from lower-alkoxy, hydroxy, lower-alkylthio, lower-alkylsulfinyl, lower-alkylsulfonyl, cyano, amino, loweralkylamino, di-lower-alkylamino or halo and $R_3$ and $R_4$ are hydrogen.

4. A method for the treatment of glaucoma which comprises administering to a patient in need of such treatment a medicament containing an effective intraocular pressure reducing amount of a compound according to claim 2 wherein;

Ar is indolyl or quinolinyl and $R_3$ and $R_4$ are hydrogen.

5. A method for the treatment of glaucoma which comprises administering to a patient in need of such treatment a medicament containing an effective intraocular pressure reducing amount of a compound according to claim 1 wherein;

$R_1$ is ArCOO and Alk is 1,2-ethylene or 1,3-propylene and Ar is phenyl or phenyl substituted by lower-alkoxy, hydroxy, lower-alkylthio, lower-alkylsulfinyl, loweralkylsulfonyl, cyano, amino, lower-alkylamino, di-loweralkylamino or halo.

* * * * *